United States Patent [19]

Truckai et al.

[11] Patent Number: 5,487,757
[45] Date of Patent: Jan. 30, 1996

[54] MULTICURVE DEFLECTABLE CATHETER

[75] Inventors: Csaba Truckai, Sunnyvale; Richard S. Jaraczewski, Livermore; Frank Nguyen, San Jose; Scott H. West, Tracy, all of Calif.

[73] Assignee: Medtronic CardioRhythm, San Jose, Calif.

[21] Appl. No.: 391,333

[22] Filed: Feb. 21, 1995

Related U.S. Application Data

[63] Continuation of Ser. No. 95,447, Jul. 20, 1993, abandoned.

[51] Int. Cl.⁶ ......................................... A61N 1/05
[52] U.S. Cl. ........................... 607/122; 607/119; 604/95; 604/280; 604/264
[58] Field of Search .................... 607/122, 123, 607/116, 119; 604/95, 264, 265, 280; 606/33, 41, 46, 48, 49, 50; 128/642, 668, 670, 695

[56] References Cited

U.S. PATENT DOCUMENTS

| | | |
|---|---|---|
| 2,498,692 | 2/1950 | Mains . |
| 3,557,780 | 1/1971 | Sato . |
| 3,582,406 | 9/1970 | Jeckel et al. . |
| 3,605,725 | 9/1971 | Bentov . |
| 4,277,168 | 7/1981 | Oku . |
| 4,586,923 | 5/1986 | Gould et al. .............. 604/95 |
| 4,677,990 | 7/1987 | Neubauer . |
| 4,718,419 | 1/1988 | Okada . |
| 4,777,955 | 10/1988 | Brayton et al. . |
| 4,860,769 | 8/1989 | Fogarty et al. ............ 607/119 |
| 4,874,371 | 10/1989 | Comben et al. . |
| 4,886,067 | 12/1989 | Palmero . |
| 4,920,980 | 5/1990 | Jackowski ................. 128/642 |
| 4,930,521 | 6/1990 | Metzger et al. . |
| 4,935,017 | 6/1990 | Sylvanowicw . |
| 4,960,134 | 10/1990 | Webster, Jr. . |
| 5,083,565 | 1/1992 | Parins . |
| 5,168,864 | 12/1992 | Shockey . |
| 5,275,151 | 1/1994 | Shockey et al. ........... 606/146 |
| 5,364,352 | 11/1994 | Cimino et al. . |

FOREIGN PATENT DOCUMENTS

| | | |
|---|---|---|
| WO93/02733 | 2/1993 | European Pat. Off. . |
| WO94/11057 | 5/1994 | European Pat. Off. . |

*Primary Examiner*—C. Fred Rosenbaum
*Assistant Examiner*—Perry E. Van Over
*Attorney, Agent, or Firm*—Townsend and Townsend and Crew

[57] ABSTRACT

An electrophysiology catheter (20) comprises a shaft (22) having a first bending stiffness and a deflectable tip (28) secured to the distal end (24) of the shaft with a second bending stiffness less than the first bending stiffness. At least one electrode (34, 36) is mounted to the tip for delivering current to or monitoring electrical activity of tissue. A manipulator wire (58) is coupled to the distal end of the deflectable tip, whereby the deflectable tip may be deflected by axial force applied to the manipulator wire. A stiffener member (66) is axially slidable relative to the tip so as to adjust the tip curvature without removing the catheter from the body. The catheter may further include a core wire (72) configured to rotate the deflectable tip about a longitudinal axis (2) without rotating the proximal end (26) of the catheter shaft, wherein the distal end of the deflectable tip remains in a substantially constant axial position, preferably in a plane perpendicular to the longitudinal axis.

35 Claims, 9 Drawing Sheets

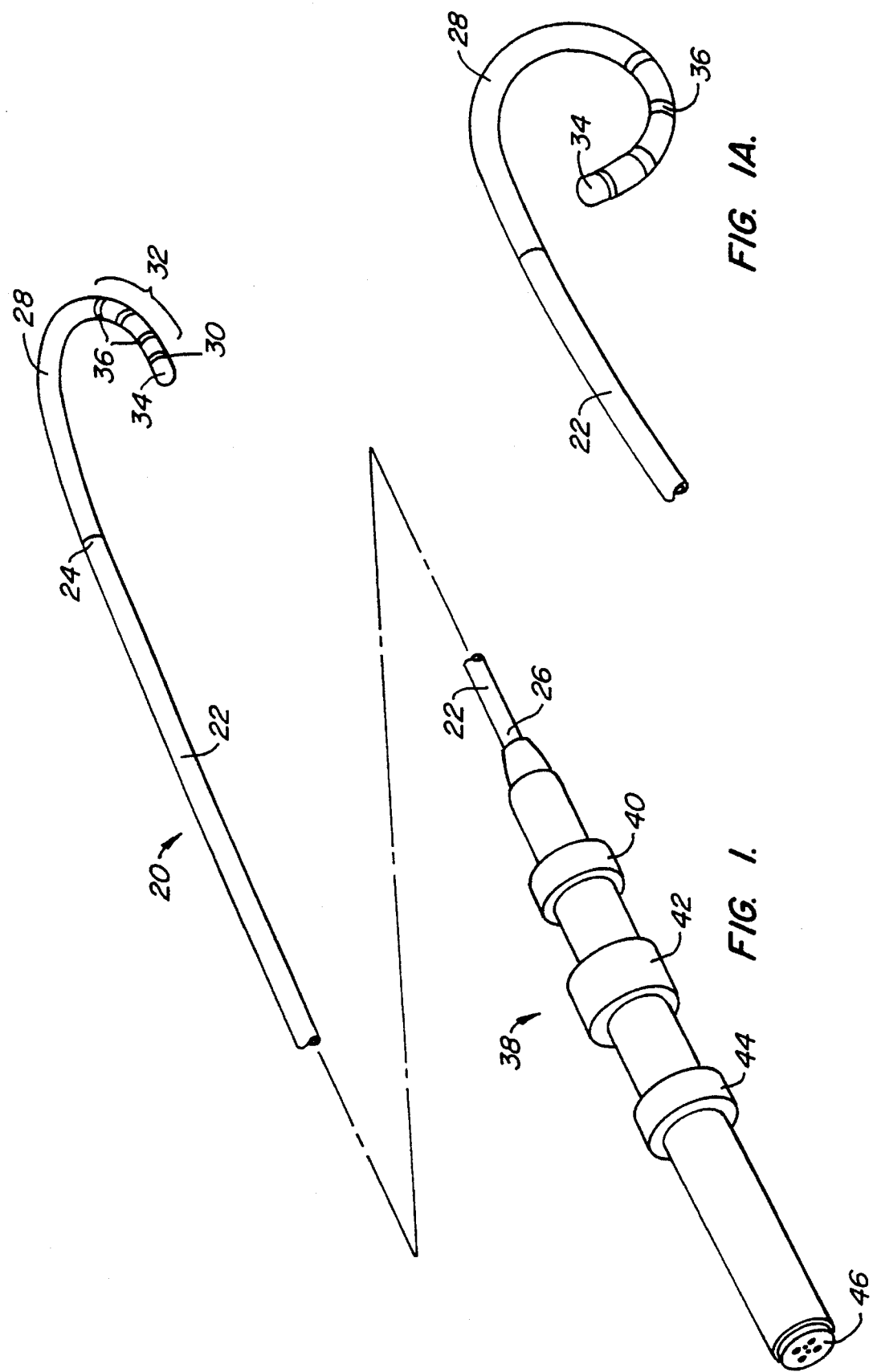

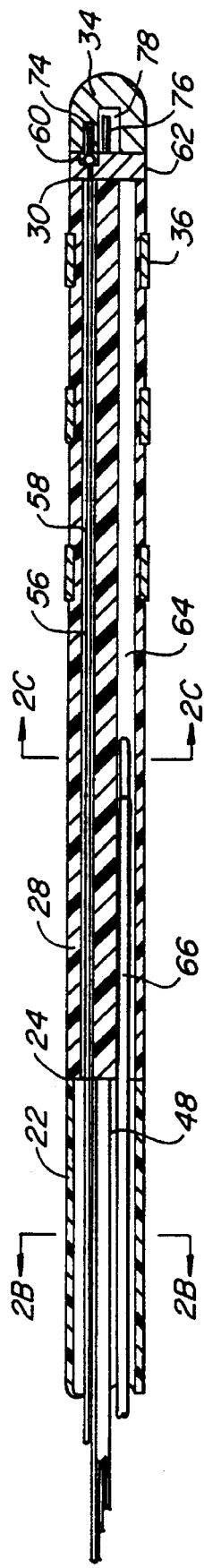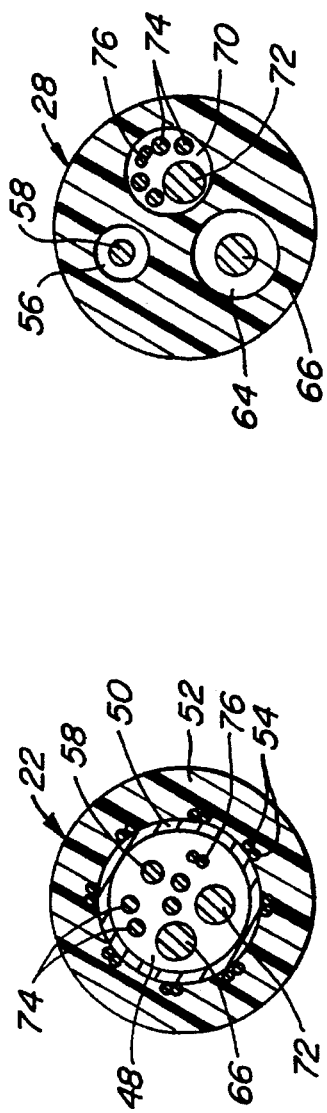
FIG. 2A.
FIG. 2C.
FIG. 2B.

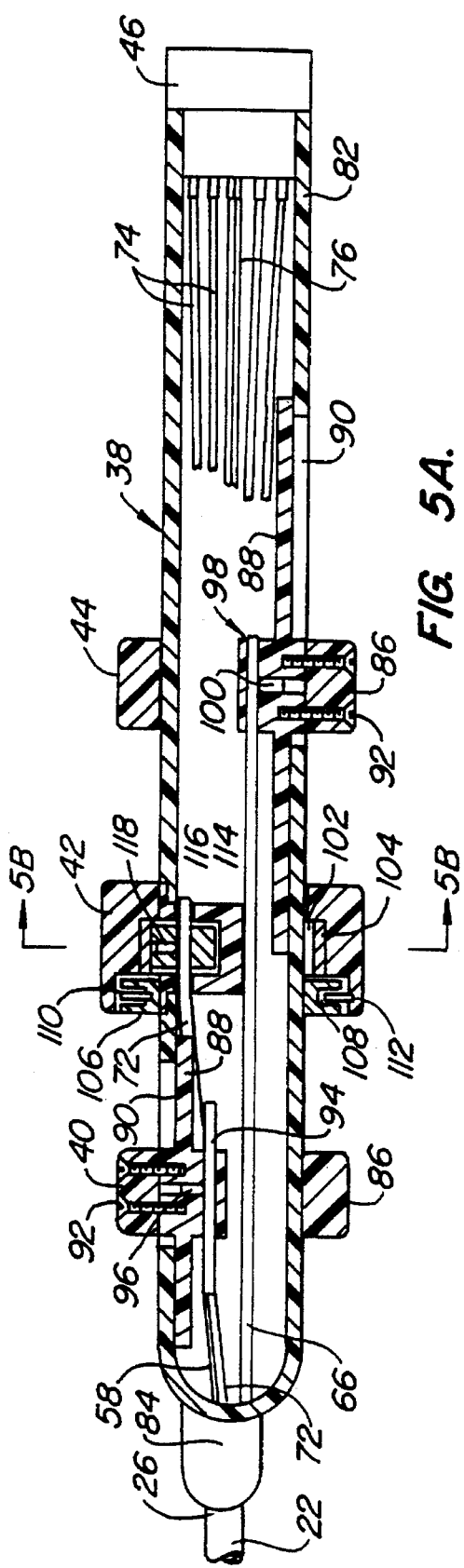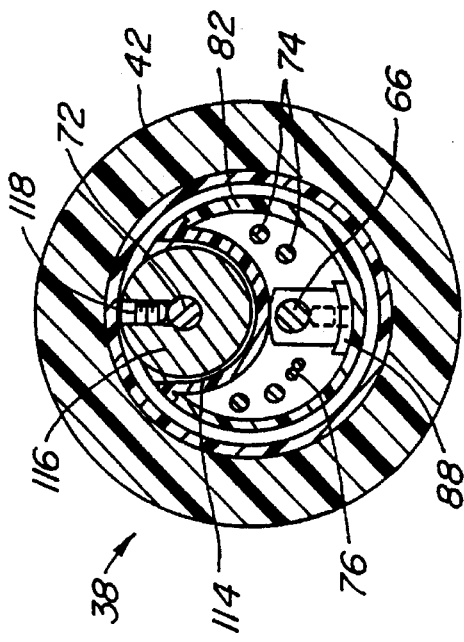
FIG. 5A.
FIG. 5B.

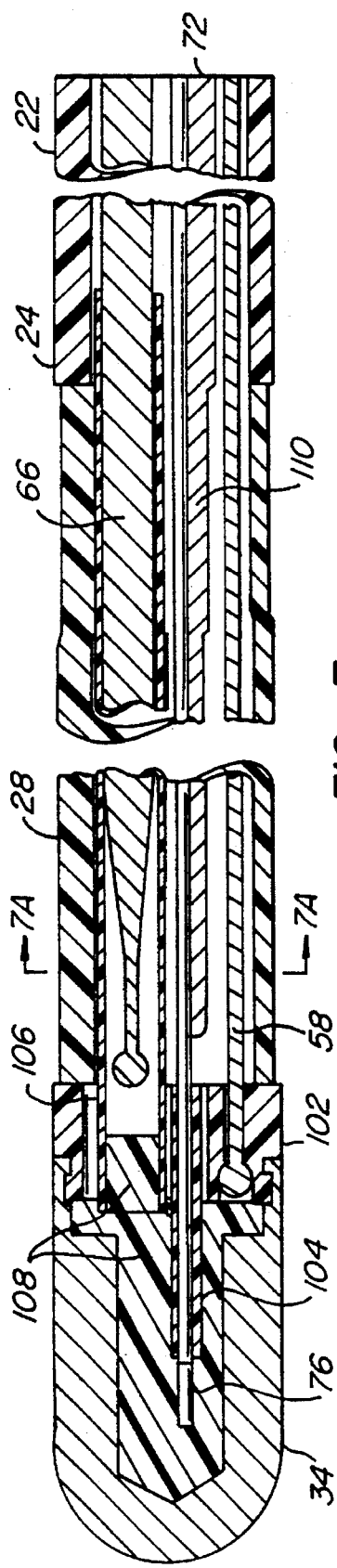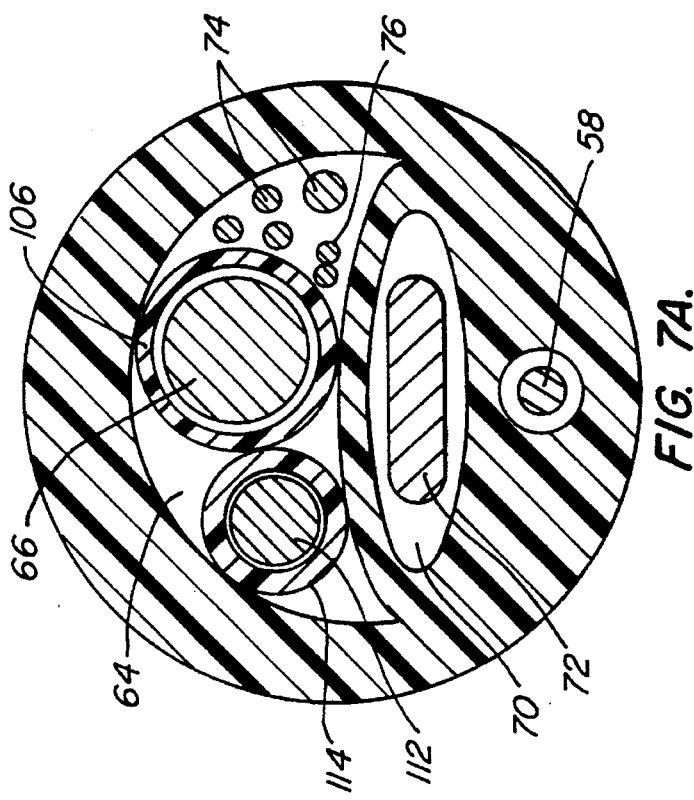
FIG. 7.
FIG. 7A.

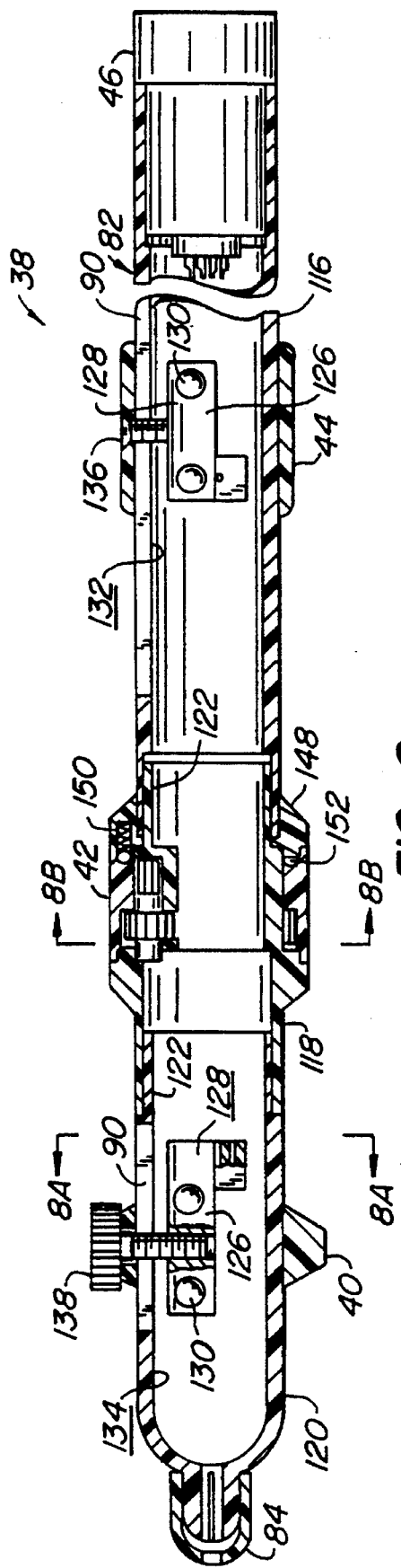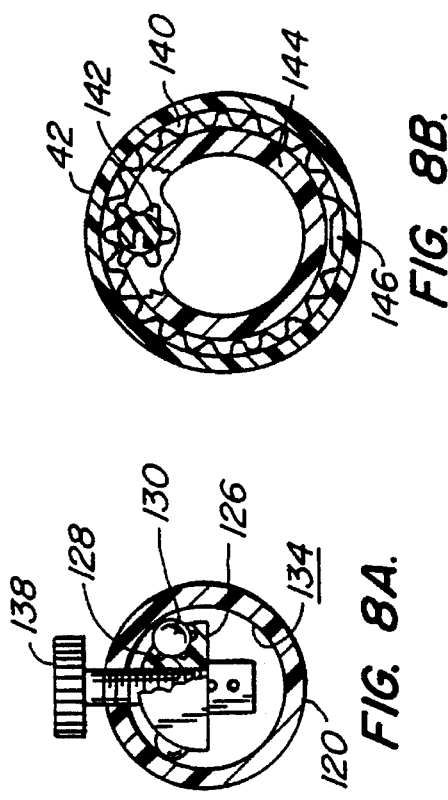
FIG. 8.
FIG. 8A.
FIG. 8B.

MULTICURVE DEFLECTABLE CATHETER

This is a continuation of application Ser. No. 08/095,447, filed Jul. 20, 1993, now abandoned.

BACKGROUND OF THE INVENTION

The present invention relates generally to steerable catheters, and more specifically to steerable electrophysiology catheters for use in mapping and ablation of the heart.

The heart includes a number of pathways which are responsible for the propagation of signals necessary for normal, electrical and mechanical function. The present invention is concerned with treatment of tachycardia, abnormally rapid rhythms of the heart caused by the presence of an arrhythmogenic site or accessory pathway which bypasses or short circuits the normal pathways in the heart. Tachycardias may be defined as ventricular tachycardias (VTs) and supraventricular tachycardias (SVTs). VTs originate in the left or right ventricle and are typically caused by arhythmogenic sites associated with a prior myocardial infarction. SVTs originate in the atria and are typically caused by an accessory pathway.

Treatment of both ventricular and supraventricular tachycardias may be accomplished by a variety of approaches, including drugs, surgery, implantable pacemakers/defibrillators, and catheter ablation. While drugs may be the treatment of choice for many patients, drugs typically only mask the symptoms and do not cure the underlying cause. Implantable devices, on the other hand, usually can correct an arrhythmia only after it occurs. Surgical and catheter-based treatments, in contrast, will actually cure the problem usually by ablating the abnormal arrhythmogenic tissue or accessory pathway responsible for the tachycardia. The catheter-based treatments rely on the application of various destructive energy sources to the target tissue including direct current electrical energy, radiofrequency electrical energy, laser energy, and the like.

Of particular interest to the present invention, are radiofrequency (RF) ablation protocols which have proven to be highly effective in tachycardia treatment while exposing the patient to minimum side effects and risks. Radiofrequency catheter ablation is generally performed after an initial mapping procedure where the locations of the arrhythmogenic sites and accessory pathways are determined. After mapping, a catheter having a suitable electrode is introduced to the appropriate heart chamber and manipulated so that the electrode lies proximate the target tissue. Radiofrequency energy is then applied through the electrode to the cardiac tissue to ablate a region of the tissue which forms part of the arrhythmogenic site or the accessory pathway. By successfully destroying that tissue, the abnormal signaling patterns responsible for the tachycardia cannot be sustained. Methods and systems for performing RF ablation by controlling temperature at the ablation site are described in co-pending application Ser. No. 07/866,683 entitled "Method and System for Radiofrequency Ablation of Cardiac Tissue," filed Apr. 10, 1992, the complete disclosure of which is hereby incorporated by reference.

Catheters designed for mapping and ablation frequently include a number of individual electrode bands mounted to the distal tip of the catheter so as to facilitate mapping of a wider area in less time, or to improve access to target sites for ablation. Such catheters are described in co-pending application Ser. No. 07/866,383, filed Apr. 10, 1992, the complete disclosure of which is incorporated herein by reference. As described in that application, it is frequently desirable to deflect tile distal tip of the catheter into a non-linear configuration such as a semicircle, which facilitates access to substantially all of the heart walls to be mapped or ablated. Such deflection may be accomplished through the use of pull wires secured to the distal tip which can be tensioned from the proximal end of the catheter to deflect the tip in the desired configuration. In addition, mapping and ablation catheters may facilitate rotational positioning of the distal tip, either by rotating the entire catheter from the proximal end, or, in the catheter described in co-pending application Ser. No. 07/866,383, by exerting torque on a core wire secured to the distal tip without rotating the catheter body itself.

Catheters utilized in radiofrequency ablation are inserted into a major vein or artery, usually in the neck or groin area, and guided into the chambers of the heart by appropriate manipulation through the vein or artery. Such catheters must facilitate manipulation of the distal tip so that the distal electrode can be positioned against the tissue region to be ablated. The catheter must have a great deal of flexibility to follow the pathway of the major blood vessels into the heart, and the catheter must permit user manipulation of the tip even when the catheter is in a curved and twisted configuration. Because of the high degree of precision required for proper positioning of the tip electrode, the catheter must allow manipulation with a high degree of sensitivity and controllability. In addition, the distal portion of the catheter must be sufficiently resilient in order to be positioned against the wall of the heart and maintained in a position during ablation without being displaced by the movement of the beating heart. Along with steerability, flexibility, and resiliency, the catheter must have a sufficient degree of torsional stiffness to permit user manipulation from the proximal end.

While mapping and ablation catheters having the forementioned deflectability and steerability have had promising results, such catheters suffer from certain disadvantages. One such disadvantage is the inability to select a desired curvature of deflection in the distal tip. In known catheters, the curvature in the distal tip is determined by the degree of bending stiffness of the distal tip and the degree of tension exerted on the pull wires coupled to it. In any one catheter, the curvature achieved in the distal tip will be the same for any given amount of tension exerted on the pull wires. Thus, if the user desires a particular shape in the distal tip, for example, a semicircle, a particular amount of tension must be exerted on the pull wires, and the semicircular curvature assumed by the distal tip will always have the same radius. Because of the variation in the size of the heart among various patients, as well as the various locations in which a mapping or ablation site may be disposed, it may be discovered during a procedure that the curvature of a given catheter is unsuitable, requiring the catheter to be removed from the patient and replaced with another catheter of suitable configuration.

A further disadvantage of known mapping and ablation catheters relates to the rotatability imparted by the core wire coupled to the distal tip. When the distal tip is deflected in a non-linear configuration, rotation of the core wire will rotate the distal tip about a longitudinal axis parallel to the catheter shaft. However, the rotation or twisting of the core wire relative to the distal tip tends to cause the distal tip to rotate in an irregular motion, wherein the distal end of the deflectable tip catheter may move significantly in longitudinal (axial) position depending upon its rotational position and also out of plane with the axis of the catheter shaft. Such irregular and variable motion defines a non-predictable path and complicates the task of accurately positioning the distal tip near a target site. The movement of the tip along such a non-predictable path hinders mapping of a circular structure, such as mitral or tricuspid valve annulus.

For these and other reasons, a steerable electrophysiology catheter for use in mapping and ablation is desired which facilitates selective adjustment of the curvature of the distal tip, and which has improved positionability, particularly in rotational positioning. More specifically, the electrophysiology catheter should permit adjustment of the curvature of the deflectable tip without removing the catheter from the patient. In addition, when the distal tip is in a deflected configuration, the catheter should be rotationally positionable without rotating its proximal end. This would permit fine control of tip positions without gross rotational movements of the shaft. Further, the end of the tip should rotate in a circle substantially within a single plane perpendicular to the catheter shaft. The catheter should further have the steerability, flexibility, resilience and torsional stiffness required for transluminal positioning in the heart and accurate guidance of the electrodes to a target site.

SUMMARY OF THE INVENTION

The catheter and a method of electrophysiological treatment which

The invention provides a steerable electropysiology have significant advantages over previous devices and methods. In particular, the device and method, of the invention facilitates selective adjustment of the curvature of flection in the tip without removing the catheter from the patient. In addition, the device and method allow the deflected tip to be rotated about a longitudinal axis without rotating the entire catheter shaft to enhance the ability for fine positioning of the tip. Also, the device and method helps to keep the tip moving in a single plane perpendicular to the shaft axis. This is particularly helpful when mapping an annulus since it provides more predictable tip movement.

In a preferred aspect of the invention, a steerable electrophysiology catheter comprises a shaft with a first bending stiffness, the shaft having a proximal end, a distal end, and an axial lumen therebetween. A deflectable tip with a second bending stiffness less than the first bending stiffness has a proximal end secured to the distal end of the shaft, a distal end, a first radially offset axial lumen and a second axial lumen in communication with the axial lumen of the shaft. At least one electrode is secured to the deflectable tip. An appropriate conductor is provided for delivering current from the proximal end of the shaft to the electrode. At least one manipulator wire extends through the axial lumen of the shaft and the first axial lumen of the deflectable tip, and has a distal end secured near the distal end of the deflectable tip and a proximal end near the proximal end of the shaft. Axial force is applied to the manipulator wire at the proximal end of the shaft to deflect the deflectable tip into a first curvature. A stiffener wire is slidably disposed in the axial lumen of the shaft and the second axial lumen of the deflectable tip. The stiffener wire has a bending stiffness such that, when advanced into a section of the tip, the stiffener wire increases the stiffness of such tip section to a value between the first bending stiffness and the second bending stiffness. The stiffener wire is moved axially relative to the deflectable tip from the proximal end of the shaft such that at least a portion of the deflectable tip assumes a second curvature. By axial translation of the stiffener wire relative to the deflectable tip, a desired degree of curvature may be selected for the deflectable tip according to the size of the heart or location of the target site to be mapped or ablated.

In an exemplary embodiment, the shaft will include reinforcement embedded in a wall thereof for reinforcing the shaft, giving it the first bending stiffness. Preferably, the reinforcement comprises a wire mesh embedded in the polymeric wall of the shaft. The shaft will preferably have a Durometer in the range of 35 D to 75 D, while the deflectable tip will have a Durometer in the range of 30 D to 55 D. The stiffener preferably becomes gradually more flexible towards its distal end, but is generally stiff enough to increase the tip stiffness when advanced into the tip.

In a further embodiment, the deflectable tip can be rotated about a longitudinal axis without rotating the proximal end of the shaft. Preferably, this is carried out using a core wire disposed in the axial lumen of the shaft and one of the axial lumens of the deflectable tip, the core wire having a distal end coupled near the distal end of the deflectable tip and a proximal end near the proximal end of the shaft. A torque is exerted on the proximal end of the core wire so as to rotate the deflectable tip. Usually, the deflectable tip will have a third axial lumen, between its proximal and distal ends in communication with the axial lumen of the shaft, in which the core wire is disposed.

In a particular embodiment, the core wire will be configured to rotate the deflectable tip while the deflectable tip is in a deflected configuration such that the distal end of the deflectable tip remains in a substantially constant longitudinal position. Preferably, the distal end of the deflectable tip will remain substantially within a plane perpendicular to the shaft. In an exemplary embodiment, the core wire has a distal portion with a cross-sectional width and thickness, the width being substantially greater than the thickness. Further, the third axial lumen in the deflectable tip may have a cross-sectional width and height, the width being substantially greater than the height. In this way, the distal portion of the core wire is trapped within the third axial lumen in the deflectable tip so that the core wire will not rotate relative to the deflectable tip. At the same time, the cross-sectional configuration of the distal portion of the core wire gives the core wire an anisotropic bending characteristic so as to maintain the core wire in alignment with the longitudinal axis, thereby maintaining the longitudinal position of the distal end as the deflectable tip is rotated. The core wire, at its proximal end, preferably has a round cross-sectional for effective torque transmission to the tip with no whip.

In a preferred embodiment, the catheter will further include a handle coupled to the proximal end of the shaft. In an exemplary embodiment, a first slide is axially slidable on the handle and is secured to the proximal end of the stiffener wire to move the stiffener wire axially. A second slide is axially slidable on the handle and is secured to the proximal end of the manipulator wire to move the manipulator wire axially. Other axial drives, including rack and pinion or a worm gear drive, could be used in lieu of the slides. In addition, a third control for lateral deflection comprises a ring gear which drives a smaller pinion gear. The pinion gear is in turn connected to the core wire. Rotating the ring gear rotates the pinion and core wire, twisting the catheter tip for lateral deflection. Various ring/pinion gear ratios may be employed to produce different tip lateral deflections for a given rotational input. Friction locks or detent elements may be applied to the first and/or second slides so as to hold the stiffener wire and/or manipulator wire in tension with the deflectable tip in a deflected configuration. Similar locks may be applied to the ring/pinion gear mechanism.

In a further preferred embodiment, the handle comprises at least two detachable sections, a first detachable section including the structure for moving the stiffener wire and a second detachable section including the structure for applying force to the manipulator wire. A third detachable section could include structure for rotating the core wire. The detachable sections will preferably comprise universal connectors for connecting the detachable sections to each other. The universal connectors preferably comprise a snap fit adapter, wherein a male snap fitting on one detachable section engages a female snap fitting in another detachable section. In this embodiment, the catheter handle is modular, allowing various detachable sections to be selectively added or removed by the manufacturer depending upon the capabilities desired in the catheter, e.g. deflectability, rotatability, or stiffener control.

In a preferred aspect of the method of the invention, a catheter is introduced through a vessel so that a distal end of the catheter is positioned in the heart, the catheter having a shaft with a first bending stiffness. An axial force is applied to a manipulator wire coupled to a deflectable tip secured to a distal end of the shaft so as to deflect the deflectable tip in a first curvature, the deflectable tip having a second bending stiffness less than first bending stiffness. A stiffener wire may be axially translated in an axial lumen of the deflectable tip such that the deflectable tip assumes a second curvature. Current is then applied through at least a first electrode on the deflectable tip to a target site on the wall of the heart, for purposes of pacing and/or ablation. For mapping, the one or more electrodes are passive and provide heart electrical signals to an ECG. In one embodiment, the stiffener is translated to a position co-extensive with only a proximal portion of the deflectable tip, whereby the proximal portion of the deflectable tip assumes a curvature which is different than a distal portion of the deflectable tip.

The method of the invention may further include rotating the deflectable tip about a longitudinal axis parallel to the shaft without rotating the proximal end of the shaft. Preferably, the deflectable tip is rotated such that a distal end of the distal tip remains in a substantially constant longitudinal position, preferably within a plane perpendicular to the shaft.

A further understanding of the nature and advantages of the invention may be realized by reference to the remaining portions of the specification and the drawings.

BRIEF DESCRIPTION OF THE DRAWINGS

FIG. 1 is a perspective view of a steerable electrophysiology catheter constructed in accordance with the principles of the present invention;

FIG. 1A is a perspective view of a distal portion of the electrophysiology catheter of FIG. 1;

FIG. 2A is a side cross-sectional view of the distal portion of the catheter of FIG. 1;

FIGS. 2B and 2C are transverse cross-sectional views taken along lines 2B—2B and 2C—2C, respectively, through the distal portion of the catheter of FIG. 2A;

FIG. 5A is a side cross-sectional view of the handle of the catheter of FIG. 1;

FIG. 5B is a transverse cross-sectional view through line 5B—5B in the handle of FIG. 5A;

FIG. 7 is an enlarged side cross-sectional view of the shaft and tip of an alternative embodiment of the invention;

FIG. 7A is a cross-sectional view taken along line 7A—7A in FIG. 7;

FIG. 8 is an enlarge side cross-sectional view of the handle of an alternative embodiment of the invention without any wires or leads;

FIGS. 8A and 8B are cross-sectional views taken along lines 8A–8B and 8B—8B.

DESCRIPTION OF SPECIFIC EMBODIMENTS

Figure 3B:
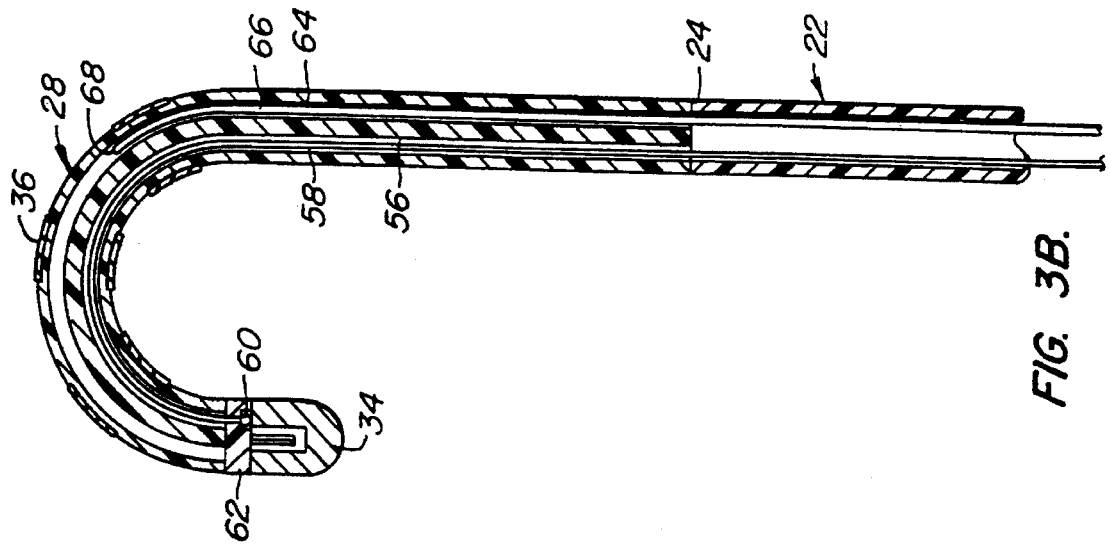
FIGS. 3A and 3B are side cross-sectional views of a distal portion of the catheter of FIG. 1 illustrating two possible tip configurations.

Electrophysiology catheters constructed in accordance with the principles of the invention will include a shaft, a deflectable tip mounted to the distal end of the shaft and a handle secured to the proximal end of the shaft. The shaft will have an axial lumen extending between its proximal and distal ends. The deflectable tip will have at least two axial lumens, one of the lumens being laterally offset from the central longitudinal axis. At least one manipulator wire will be disposed in the offset axial lumen of the deflectable tip and the axial lumen of the shaft, and will be coupled at its distal end to the distal end of the deflectable tip. Means will be coupled to the handle for applying an axial force to the manipulator wire so as to deflect the distal end of the deflectable tip. The manipulator wire may be configured for either tension or compression to deflect the tip, but usually will be a flexible wire of stainless steel or the like for applying a tensile force to pull on the distal end of the deflectable tip. Such application of tension will cause the deflectable tip to assume a curvature based largely on the degree of bending stiffness of the deflectable tip. Both the shaft and the deflectable tip will have a bending stiffness which is low enough to allow the catheter to be transluminally positioned through a tortuous path into the heart. However, the deflectable tip will have a bending stiffness substantially less than that of the shaft so that the shaft has sufficient column strength to remain substantially undeflected when the manipulator wire is tensioned, and the deflectable tip is sufficiently flexible for deflection into a non-linear configuration of small curvature.

It is desirable to have a smooth transition in stiffness at the junction of the distal end of the shaft and the proximal end of the flexible tip to prevent kinking. This can be accomplished by varying the stiffness of one or both of the flexible tip and the shaft ill the regions adjacent their junction, and by varying the stiffness of the stiffener wire along its length.

The catheter will further include a stiffener wire slidably disposed in the axial lumen of the shaft and an axial lumen of the deflectable tip. Means will be provided on the handle for sliding the stiffener wire relative to the deflectable tip, thereby changing the bending stiffness of the deflectable tip according to the position of the stiffener wire. In this way, the deflectable tip may be given a desired curvature by appropriate tensioning of the manipulator wire and/or longitudinal adjustment of the stiffener wire.

In a further aspect of the invention, a steerable electrophysiological catheter will include means for rotating the distal end of the deflectable tip without rotating the proximal end of the shaft, whereby the distal end of the deflectable tip remains in a substantially constant longitudinal position. Preferably, during such rotation, the distal end of the deflectable tip will remain substantially within a plane perpendicular to the shaft. In one embodiment, the core wire will have a distal portion having a cross-sectional width which is substantially greater than its thickness, giving the core wire a non-isotropic bending characteristic in the distal portion. In this way, application of torque on the proximal end of the core wire causes the distal portion of the core wire to rotate only about the longitudinal axis, without variation in longitudinal (axial) or radial position. The distal end of the deflectable tip thereby remains in a substantially constant longitudinal position as the core wire is rotated. The remainder of the core wire, other than that at the tip, is preferably round for optimal torque transmission. If desired, the core wire diameter could taper along its length.

Referring now to FIG. 1, electrophysiology catheter 20 includes a shaft 22 having a distal end 24 and a proximal end 26. A deflectable tip 28 is fixed to distal end 24 of shaft 22. Deflectable tip 28 has a distal end 30, and has a plurality of electrodes 32 including a tip electrode 34 and electrode bands 36.

A handle 38 is secured to proximal end 26 of shaft 22. Handle 38 includes a tip deflection slide 40, core wire torquer ring 42 and curvature adjustment slide 44, as well as an electrical connector 46, all described more fully below. As illustrated in FIG. 1A, deflectable tip 28 may be deflected from a straight configuration into a variety of shapes and curvatures, up to at least 270° relative to shaft 22, by adjustment of tip deflection slide 40, curvature adjustment slide 44 and core wire torquer ring 42.

Referring now to FIGS. 2A–2C, shaft 22 has an axial lumen 48 between its proximal and distal ends. The preferred construction of shaft 22 includes a polyimide or ULTEM™ inner tube 50 surrounded by an extruded topcoat 52 of a flexible polymer such as PEBAX. To add torsional and bending stiffness to shaft 22, a braided reinforcement 54, usually stainless steel, is embedded in topcoat 52. With this construction, topcoat 52 will have a Durometer reading preferably in the range of 35 D to 75 D.

Deflectable tip 28 will preferably be a unitary extrusion of a flexible polymer such as PEBAX with a Durometer reading in the range of 30 D to 55 D. Tip 28 may include internal reinforcement using materials such as polyimide or ULTEM. In a preferred embodiment, the deflectable tip will have three axial lumens extending from its proximal end to its distal end, all in communication with axial lumen 48 in shaft 22. A first axial lumen 56 will be radially offset from the central longitudinal axis of the deflectable tip through which a manipulator wire 58 is disposed. Manipulator wire 58 is coupled at its distal end 60 to an anchor plate 62 at the distal end 30 of deflectable tip 28. Preferably, manipulator wire has a diameter of about 0.15 mm and distal end 60 of the manipulator wire comprises a ball or similar structure for retaining the distal end against anchor plate 62. In a preferred embodiment, axial lumen 56 will be radially offset from the central axis of deflectable tip 28 by an amount equal to approximately 40% to 95% of the radius of the deflectable tip. In an exemplary embodiment, deflectable tip 28 and shaft 22 have a diameter in the range of 5 French (1.65 mm/0.065") to 7 French (2.34 mm/0.092"), with axial lumen 56 being offset in the range of 0.66 mm (0.026") to 2.21 mm (0.087") from the central axis.

Deflectable tip 28 includes a second axial lumen 64 in which a stiffener wire 66 is slidably disposed. In a preferred embodiment, stiffener wire 66, when advanced into tip 28, will give tip 28 and wire 66 a combined bending stiffness greater than that of deflectable tip 28 alone, but less than the bending stiffness of shaft 22. In one embodiment, stiffener wire 66 comprises a stainless steel wire with a diameter which ranges from 0.64 mm (0.025") at its proximal end to 0.46 mm (0.018") at its distal end for a deflectable tip 28 with diameter of 2.34 mm (0.092").

Figure 3A:
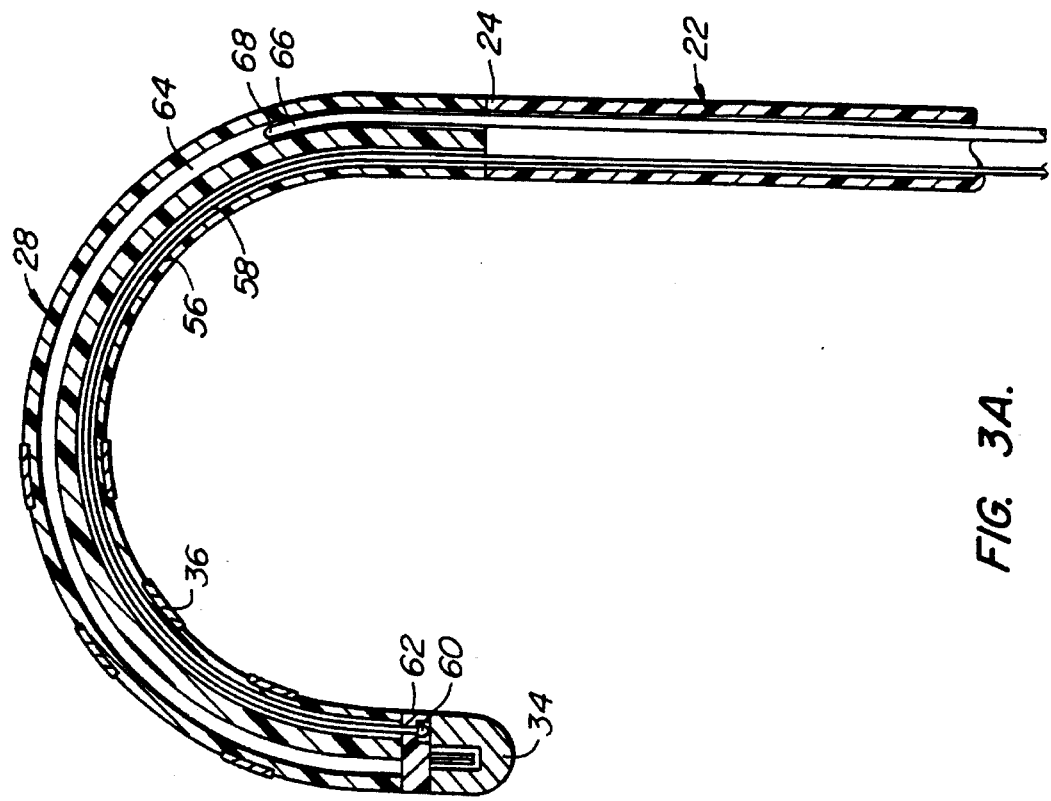

As illustrated in FIGS. 3A and 3B, the curvature imparted to deflectable tip 28 may be selectively adjusted by axially translating stiffener wire 66 within lumen 64, while exerting tension on manipulator wire 58. In the example of FIG. 3A, stiffener wire 66 has been positioned such that its distal end 68 extends into a proximal portion of lumen 64 in deflectable tip 28. The proximal portion of the deflectable tip in which the stiffener wire is disposed therefore has a bending stiffness which is greater than the remaining distal portion of the deflectable tip. By exerting tension on manipulator wire 58, deflectable tip 28 is deflected into a curvature dependent upon the longitudinal position of stiffener wire 66 and the degree of tension applied to the manipulator wire. In FIG. 3B, stiffener wire 66 has been extended distally so that the distal end 68 is closer to the distal end of the deflectable tip. The proximal portion of axial lumen 64 occupied by the stiffener wire is now larger than in the example of FIG. 3A, giving the distal portion of deflectable tip 28 a smaller radius of curvature for a given degree of tension on manipulator wire 58. In this way, when the catheter of the invention has been positioned in the heart, the configuration of the tip can be selectively adjusted to impart the desired curvature and shape to the deflectable tip as appropriate for the size and location of the area to be mapped and/or ablated.

In a preferred embodiment, stiffener wire 66 is TEFLON®-coated stainless steel and has a diameter over most of its length of about 0.51 mm (0.020"), tapers down over a length of about 25 mm (1.0") to a 0.15 mm (0.006") diameter for the last 13 mm (0.5") of length. The tip of wire 66 also preferably has a ball, of a 0.38 mm (0.015") maximum diameter, welded thereto.

Referring again to FIGS. 2A–2C, deflectable tip 28 further includes a third axial lumen 70 through which a core wire 72 along with electrode wires 74 and thermocouple wires 76 extend. Each of electrode wires 74 is connected to one of electrodes 34, 36. Thermocouple wires 76, typically copper and constantan, extend into an aperture 78 in tip electrode 34 where they are anchored with high temperature adhesive. (As an alternative to stiffener wire 66, an axially extendable tubular stiffener surrounding core wire 72 could be used.)

Core wire 72 extends distally through axial lumen 70 and, in one embodiment, is fixed at its distal end to anchor plate 62. Catheters utilizing such a core wire construction are disclosed in co-pending application Ser. No. 07/866,383, the complete disclosure of which has been incorporated herein by reference.

Figure 4A:
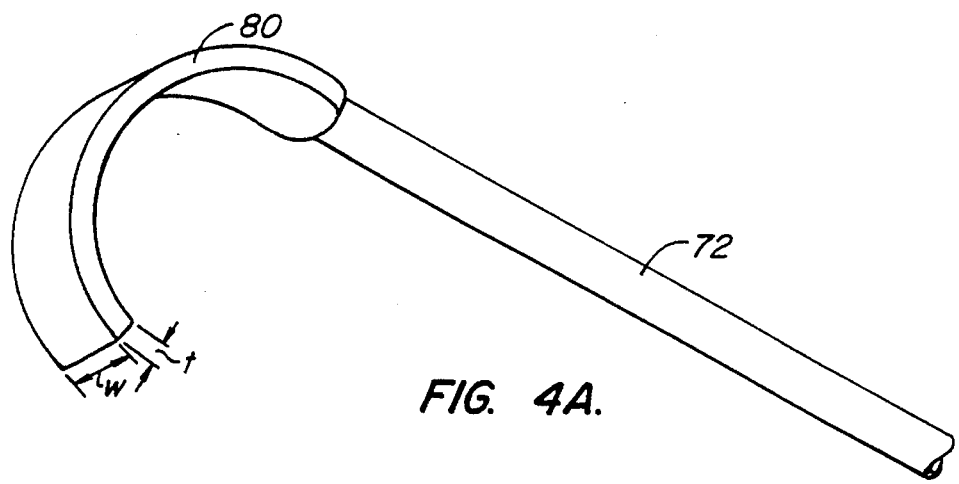
FIG. 4A is a perspective view of a distal portion of a preferred embodiment of the core wire in the catheter of FIG. 1.
Figure 4B:
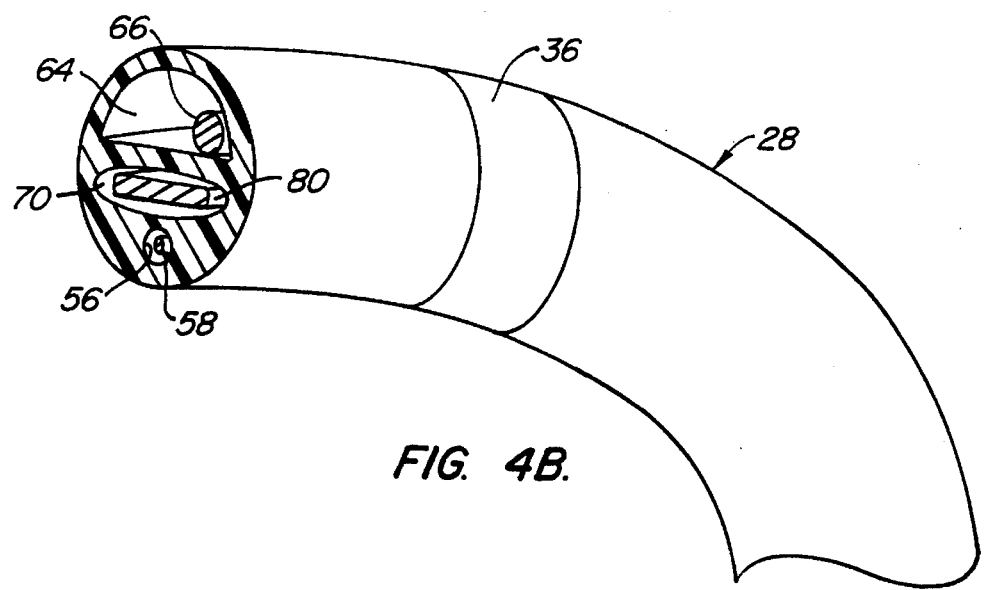
FIG. 4B is a perspective view showing a cross-section of a distal portion of the catheter of FIG. 1 with the core wire of FIG. 4A.
Figure 4C:
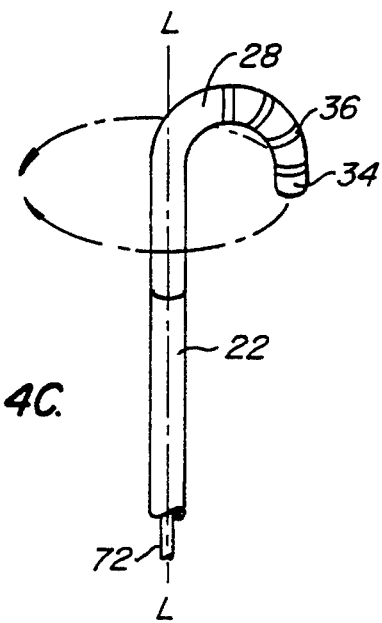
FIG. 4C is a perspective view of a distal portion of the catheter of FIG. 1 with the core wire of FIG. 4A, illustrating the rotational motion of the deflectable tip imparted by the core wire.

In an alternative preferred embodiment, illustrated in FIGS. 4A–4C, core wire 72 has a distal portion 80 configured to give the core wire an anisotropic bending characteristic in at least the distal portion. The remainder of core wire 72 has a round cross section for optimal torque transmission. In one embodiment, distal portion 80 is rectangular in cross section with a width W substantially greater than its thickness T. In this way, the bending stiffness of distal portion 80 will be substantially greater about one transverse axis than about a second perpendicular transverse axis. When torque is applied to the proximal end of core wire 72, the configuration of Fig. 4A will minimize any rotation or twisting of the distal portion 80 relative to the deflectable tip when the deflectable tip is in a deflected configuration. As a result, as shown in FIG. 4C, deflectable tip 28 may be rotated about a longitudinal axis L such that tip electrode 34 remains in a substantially constant longitudinal (axial) position relative to shaft 22 for various rotational positions, and preferably remains substantially within a plane perpendicular to longitudinal axis L. Core wire 72 changes from the round cross-section to the flattened rectangular cross section at distal portion 80 since distal portion is responsible for rotating bent tip 28 as suggested in FIG. 4C. That is, the round cross-sectional shape is best for torque transmission while the flattened rectangular cross-sectional shape of distal portion 80 is best for resisting bending as tip 28 is rotated as in FIG. 4C. To ensure the maximum bending stiffness of distal portion 80 as tip 28 is rotated about axis L, width W is oriented in a plane lying perpendicular to a radius extending from axis L to manipulator wire 58.

In one preferred embodiment, core wire 76 is TEFLON®-coated stainless steel having a diameter over most of its length of about 0.64 mm (0.025"). Core wire 76 has a transition region towards tip 28 where over a length of about 7.6 cm (3.0"), the diameter decreases from about 0.64 mm to about 0.46 mm (0.018"). The next about 25 cm (10.0") of core wire 76 has a constant 0.46 mm diameter. The remaining approximately 12 cm (4.7") of core wire 76 is flattened in two stages. The first stage, about 2.5 cm (1.0") long, is flattened to about 0.30 mm (0.012") thick by 0.58 mm (0.023"). The distal-most 9.2 cm (3.625") is flattened to about 0.20 mm (0.008") thick by about 0.79 mm (0.031").

In a further preferred embodiment, axial lumen 70 in deflectable tip 28 will have a configuration complementary to that of the distal portion 80 of core wire 72 so as to prevent rotational movement of distal portion 80 within lumen 70 relative to the deflectable tip. In an exemplary embodiment, axial lumen 70 has a cross sectional width (parallel to width W of distal portion 80) which is substantially larger than its height (parallel to thickness T of distal portion 80). In this way, distal portion 80 of the core wire is entrapped within axial lumen 70 to prevent relative rotational movement thereof.

The proximal end of rectangular distal portion 80 of core wire 72 is locked in place in tip 28, such as by heat fusing. This allows core wire 72 to transmit the torquing force to tip 28 at this point. This further helps to prevent "flipping" of core wire 72 as tip 28 is rotated. If desired, distal portion 80 of core wire 72 could extend through most but not all of tip 28 and would not be secured to anchor plate 62. This allows core wire 72 to move longitudinally within axial lumen 70 when tip 28 is deflected by manipulator wire 58 to improve bending characteristics.

Referring now to FIGS. 5A and 5B, handle 38 will be described in greater detail. Handle 38 includes a housing 82, usually cylindrical in shape, constructed of a rigid material such as ABS, nylon, polycarbonate or polystyrene. Shaft 22 is fixed to housing 82 by means of a mechanical grip or an adhesive and incorporating a strain relief 84. Deflection adjustment slide 40 and curvature adjustment slide 44 have similar construction. Slides 40, 44 include an outer ring 86 disposed about the periphery of housing 82 so as to slide axially thereon. Slots 90 extend axially along housing 82 and are in communication with the interior of the housing. Slide backing plates 88 are disposed in the interior of housing 82 and, in this embodiment, longer than slots 90. Rings 86 are fixed to slide backing plates 88 by means of screws 92, whereby friction between backing plates 88 and the interior of housing 82 may be increased by tightening screws 92. With respect to deflection adjustment slide 40, a hypotube 94 is secured to slide backing plate 88, and manipulation wire 58 extends through hypotube 94. Wire 58 and hypotube 94 are joined such as by crimping, or using an adhesive. A screw 96 in backing plate 88 is tightened to frictionally retain hypotube 94. In the case of curvature adjustment slide 44, stiffener wire 66 extends directly through a bore 98 in slide backing plate 88 and is retained therein by a set screw 100. It may be seen that by sliding deflection adjustment slide 40 and curvature adjustment slide 44 axially along slots 90, the deflection of the deflectable tip 28 may be appropriately adjusted. The deflected shape of the tip may be retained by appropriate tightening of screws 92 so that backing plates 88 frictionally engage the interior of housing 82. Sliders 88 act to cover slots 90 to prevent fluid ingress. If desired, flexible external bellows or low Durometer wipers can be used to cover slots 90 allowing the use of shorter sliders 88. Instead of sliders 88, other types of drivers, such as rack and pinion or worm gear drivers, could be used.

Core wire torquer ring 42 is rotatably coupled to housing 82. Torquer ring 42 defines an annular aperture 102 in which is disposed a friction ring 104 of rubber or other high friction material secured to the torquer ring. A limiter ring 106 is fixed to the periphery of housing 82 and defines an annular channel 108. A pin 110 is fixed in a radial position in annular channel 108 and is configured to engage a pin 112 fixed to torquer ring 42 extending radially inward within annular channel 108. Engagement of pins 110, 112 with each other thereby limits the rotational motion of torquer ring 42.

Housing 82 includes a partially cylindrical portion 114, see FIG. 5B, for supporting an inner roller 116. Core wire 72 is fixed to inner roller 116 by means of a set screw 118. Inner roller 116 preferably has a knurled outer surface to frictionally engage friction ring 104 bonded to torquer ring 42. In this way, rotation of torquer ring 42 rotates inner roller 116, thereby exerting torque on the proximal end of core wire 72. If desired, and with appropriate structural modifications, the functions of slider 40 and ring 42 could be combined into a single control.

Alternatively, torquer ring 42 may comprise a ring gear having drive teeth for engaging gear teeth (not shown) on the outer surface of inner roller 116, as described in co-pending application Ser. No. 08/085,220, attorney docket no. 14875-3-1, entitled "Shapable Handle for Steerable Electrode Catheter," filed Jun. 29, 1993, the complete disclosure of which is incorporated herein by reference. A rotational travel stop for such a rotary drive could be provided by filling in one or more teeth.

Electrode wire 74 and thermocouple wire 76 extend from shaft 22 through the interior of housing 82 and are coupled to electrical connector 46. Connector 46 is configured for connection to a radiofrequency ablation generator, such as that described in co-pending application Ser. No. 07/866, 683, the disclosure of which has been incorporated herein by reference. Connector 46 can also be connected to an ECG machine for mapping.

Figure 6A:
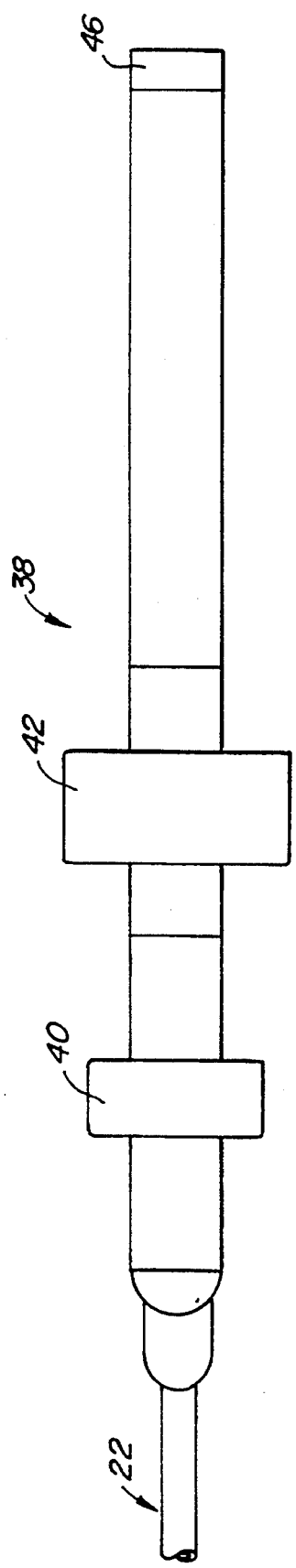
FIGS. 6A—6C are schematics of the handle of the catheter of FIG. 1, illustrating various configurations of the detachable handle sections.
Figure 6B:
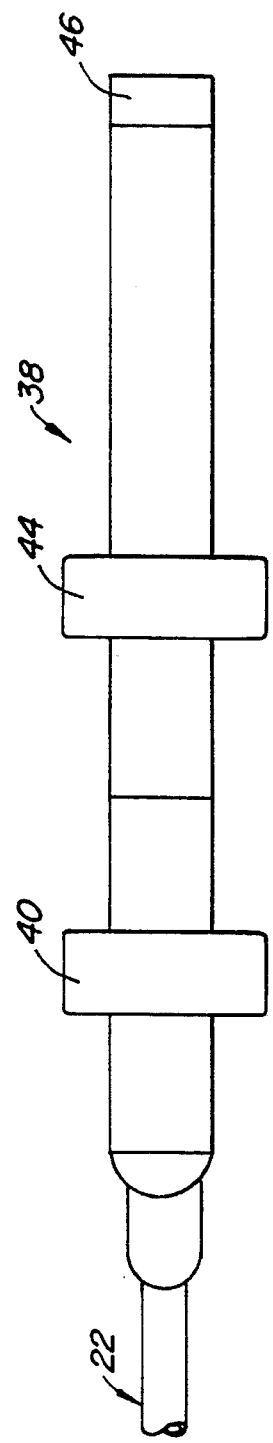
Figure 6C:
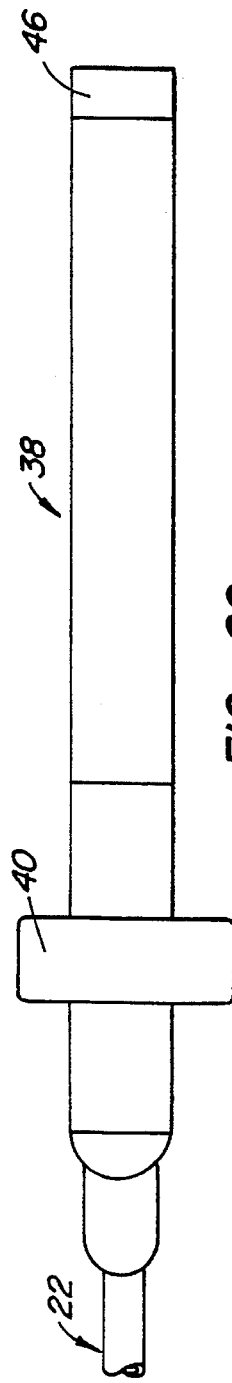

Handle 38 preferably has a modular construction facilitating easy interchange of actuator components, depending upon the capabilities desired in the catheter. As illustrated schematically in FIGS. 6A–6C, handle 38 will preferably comprise at least two detachable sections, each section having a universal fitting for attachment to one of the other sections. Each detachable section will include at least one of the actuators for steering and deflecting the distal tip of the catheter, i.e., tip deflection slide 40, torquer ring 42 or curvature adjustment slide 44. In this way, handle 38 may be assembled to include only the components desired by a particular user, thereby minimizing the size, cost and complexity of the device.

Where deflection, rotation and curvature control are all desired in the catheter, detachable segments having the tip deflection slide 40, torquer ring 42, curvature adjustment slide 44 as well as electrical connector 46 will all be interconnected by means of snap fittings, as shown in FIGS. 1 and 5A. Alternative configurations are illustrated in FIG. 6A– 6C. In a first alternative configuration, handle 38 is provided only with the detachable sections having tip deflection slide 40, torquer ring 42 and connector 46. In the alternative embodiment of FIG. 6B, torquer ring 42 is left out, with tip deflection slide 40 being coupled with curvature adjustment slide 44, along with connector 46. In a third embodiment, shown in FIG. 6C, only tip deflection slide 40 is provided in conjunction with connector 46.

FIG. 7 is a view, similar to that of FIG. 2A, of an alternative embodiment of the invention with like reference numerals referring to like parts. The embodiment of FIG. 7 differs from the embodiment of FIG. 2A primarily with reference to the following. An anchor plate 102 is used to couple electrode tip 34 to tip 28. A polyimide tubing 104 is used to guide the passage of the distal ends of thermocouple wires 76 into tip electrode 34. Another polyimide tubing 106 is used to surround that portion of stiffener wire 66 within tip 28. The interior of tip electrode and the distal end of polyimide tubing 106 are both filled with an electrically insulating, thermally conductive adhesive 108. A section 110 of core wire 72 is thermally fused within axial lumen 70 formed in tip 28 adjacent distal end 24 of shaft 22. As can be seen best in FIG. 7A, a wire stiffener 112 is housed within a polyimide tubing 114 within second axial lumen 64. Wire stiffener 112 extends from anchor plate 102 proximally to a point where stiffener overlaps core wire 72. Stiffener 112 is used to help prevent kinking of tip 28 since core wire 72, in this embodiment, does not extend completely to tip electrode 34 or adapter 102.

Figure 9:
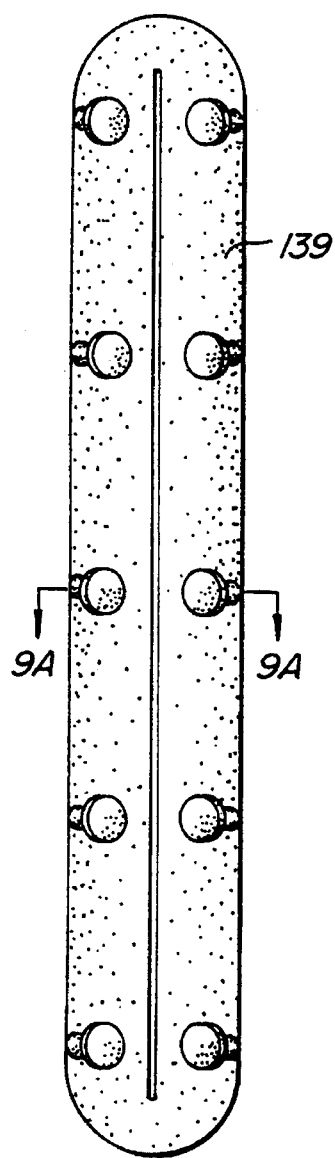
FIGS. 9 and 9A are bottom plan and side cross-sectional views of a wiper-type seal for use with the handle of FIG. 8.
Figure 9A:
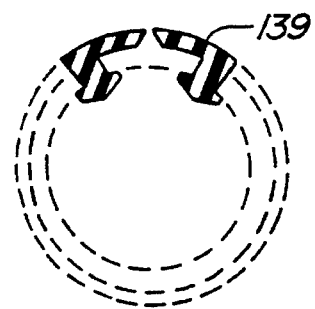

FIG. 8 illustrates an alternative embodiment of handle 38, again with like reference numerals referring to like elements. Housing 82 is shown to include three housing sections 116, 118 and 120. Housing section 118 is mounted to housing sections 116 and 120 using complementary snap-fit joints 122 so that, if desired, housing section 116 can be mounted directly to housing section 120. Instead of backing plates 88, deflection adjustment slider 40 and curvature adjustment slider 44 use front and rear ball sliders 122, 124. Ball sliders 122, 124 each have a semi-cylindrical base 126 having four recesses in its curved outer surface 128 and within which steel balls 130 are mounted. Steel balls ride against the inside surfaces 132, 134 of housing sections 116, 120, respectively. The ball shapes may be formed as integral extensions of base 126. Tightening screws 136, 138 permits the user to adjust the friction between sliders 40, 44 and housing 82. It has been found that ball sliders 122, 124 provide smooth and highly adjustable frictional characteristics. While not shown in this embodiment, fluid shields, such as of the type shown in FIGS. 5A and 5B created by backing plates 88, or by an external bellows type fluid shields, or using external wipers 139 shown in FIGS. 9 and 9A, could be used to cover slots 90 in the embodiment of FIG. 8.

Torquer ring 42 includes an integrally formed internal ring gear 140 which mates with a pinion 142 carried by a torquer housing 144. The proximal end of core wire 72 (not shown in FIG. 8) is secured to pinion 142. Rotation of torquer ring 42 about housing section 118 causes pinion 142 to rotate about its axis as it engages ring gear 140. Ring gear 140 has a missing or filled in tooth 146 to limit the total rotary movement of torquer ring 42, to just under 180° in each direction. Ring gear 140 and pinion 142 have a 4 to 1 ratio so that pinion rotates almost two complete revolutions in either direction. Due to friction and other losses, this causes distal portion 80 of core wire 72 to rotate about 180° in either direction.

Housing section 118 includes a proximal portion 148 which carries a ball detent 150. Ball detent 150 engages a series of indentations 152 formed in the proximally facing edge of torquer ring 42. In the preferred embodiment there are 72 indentations 152 spaced around the periphery of torquer ring 42. Ball detent 150 not only keeps core wire 72 in the desired rotary orientation, but also helps making fine adjustments in the rotary orientation of the core wire 72 and thus of tip 28.

In a preferred aspect of the method of the invention, catheter 20 is transluminally positioned through a blood vessel so that the deflectable tip 28 is within the heart. An axial force is then applied to manipulator wire 58 by sliding tip deflection slide 40 proximally so as to laterally deflect deflectable tip 28 in a first curvature. To further adjust the curvature of the deflectable tip to an optimum configuration, stiffener wire 66 is translated axially relative to the deflectable tip by sliding curvature adjustment slide 44 distally. When the desired degree of curvature has been obtained, deflectable tip 28 may be further positioned rotationally by rotating torquer ring 42, thereby exerting torque on core wire 42 which rotates the deflectable tip about a longitudinal axis. Due to the constructions of core wire 72, described above, tip electrode 3.4 at the distal end of the deflectable tip will remain in a substantially constant longitudinal position relative to handle 38 and shaft 22, preferably substantially within a plane perpendicular to shaft 22. When the electrodes on the deflectable tip have been positioned near a desired target site, radiofrequency current is delivered through connector 46 and electrode wires 74 to electrodes 34, 36, through which current is conducted to the heart tissue to perform ablation. Mapping can be accomplished when catheter 20 is used with an ECG. Advantageously, the catheter may be repositioned and reconfigured in various shapes and curvatures without removing the deflectable tip from the heart, due to the ability to adjust the axial position of stiffener wire 66 in deflectable tip 28. Thus, using the catheter of the invention, virtually any area of the heart may be mapped and/or ablated without removal or interchange of devices.

While the above is a complete description of the preferred embodiments of the invention, various alternatives, modifications and equivalents may be used. Therefore, the above should not be taken as limiting the scope of the invention, which is defined by the appended claims.

What is claimed is:

1. A steerable electrophysiology catheter comprising:
    a shaft with a first bending stiffness, the shaft having a proximal end, a distal end, and an axial lumen therebetween;

a deflectable tip with a second bending stiffness less than the first bending stiffness, the deflectable tip having a proximal end secured to the distal end of the shaft, a distal end and an axial tip lumen in communication with the axial lumen of the shaft;

at least one electrode secured to the deflectable tip;

means for conducting current between the proximal end of the shaft and the electrode;

a manipulator wire extending through the axial lumen of the shaft and the tip lumen, the manipulator wire having a distal end secured to the distal end of the deflectable tip and a proximal end near the proximal end of the shaft;

an elongate, flexible stiffener element slidably disposed in the axial lumen of the shaft and the tip lumen, the stiffener element having a third bending stiffness;

means at the proximal end of the shaft for applying axial force to the manipulator wire to deflect the deflectable tip into a first curvature; and means at the proximal end of the shaft for axially moving the stiffener element relative to the deflectable tip such that at least a portion of the deflectable tip assumes a second curvature.

2. The catheter of claim 1 wherein the shaft further includes means embedded in a wall thereof for reinforcing the shaft.

3. The catheter of claim 2 wherein the reinforcing means comprises a wire mesh.

4. The catheter of claim 1 wherein the stiffener element is a stiffener wire.

5. The catheter of claim 1 further comprising means for rotating the deflectable tip about a longitudinal axis without rotating the proximal end of the shaft.

6. The catheter of claim 1 further comprising:

a core wire disposed in the axial lumen of the shaft and the tip lumen, the core wire having a distal end rotatably driveably coupled to the deflectable tip and a proximal end near the proximal end of the shaft; and means for exerting torque on the proximal end of the core wire so to rotate the deflectable tip about a longitudinal axis without rotating the proximal end of the shaft.

7. The catheter of claim 6 wherein the proximal end of the tip is secured to the core wire so to transmit torque from the core wire to the tip at the proximal end of the tip.

8. The catheter of claim 6 wherein the axial tip lumen of the deflectable tip comprising a first, radially offset, axial tip lumen housing the manipulator wire, a second axial tip lumen housing the stiffener element, and a third axial tip lumen, the core wire being disposed in the third axial tip lumen.

9. The catheter of claim 8 wherein the core wire has a distal portion having a cross-sectional width and thickness, the width being substantially greater than the thickness.

10. The catheter of claim 9 wherein the distal portion of the core wire has first and second sections with first and second cross-sectional widths and thicknesses.

11. The catheter of claim 9 wherein the third axial lumen has a cross-sectional width and height, the width being substantially greater than the height.

12. The catheter of claim 1 wherein the shaft includes an outer surface layer having a Durometer reading in the range of 35 D to 75 D.

13. The catheter of claim 1 wherein the deflectable tip includes an outer surface layer having a Durometer reading in the range of 30 D to 55D.

14. The catheter of claim 1 wherein the deflectable tip is deflectable about an angle of at least about 360° relative to the shaft.

15. The catheter of claim 1 further comprising a handle secured to the proximal end of the shaft, wherein the means for moving the stiffener wire and the means for applying force to the manipulator wire are coupled to the handle.

16. The catheter of claim 15 wherein the means for moving the stiffener wire comprises a first slide axially slidable on the handle and secured to the proximal end of the stiffener wire.

17. The catheter of claim 15 wherein the means for applying force to the manipulator wire comprises a slide axially slidable on the handle and secured to the proximal end of the manipulator wire.

18. The catheter of claim 17 further comprising means in the handle for adjustably applying friction to the slide so as to hold the manipulator wire in tension.

19. The catheter of claim 15 wherein the handle comprises at least two detachable sections, a first detachable section including the means for moving the stiffener wire and a second detachable section including the means for applying force to the manipulator wire.

20. The catheter of claim 19 wherein the handle further comprises a third detachable section including means for rotating the deflectable tip about a longitudinal axis without rotating the proximal end of the shaft.

21. The catheter of claim 19 wherein the first and second detachable sections comprise universal means for connecting the detachable sections to each other.

22. The catheter of claim 21 wherein the universal connecting means comprises a snap fit coupling.

23. A method of electrophysiological treatment comprising:

introducing a catheter through a vessel so that a distal end of the catheter is positioned in the heart, the catheter having a shaft with a first bending stiffness;

applying axial force to a manipulator wire coupled to a deflectable tip secured to a distal end of the shaft to deflect the deflectable tip in a first curvature, the deflectable tip having a second bending stiffness less than the first bending stiffness;

axially translating a stiffener wire slidably disposed in an axial lumen of the deflectable tip such that the deflectable tip assumes a second curvature; and electrically operating at least a first electrode on the deflectable tip associated with a target site on a wall of the heart.

24. The method of claim 23 wherein the electrically operating step is carried out by applying a current through at least the first electrode.

25. The method of claim 23 wherein the stiffener wire is translated to a position coextensive with only a proximal portion of the deflectable tip, whereby the proximal portion of the deflectable tip assumes a curvature which is different than a distal portion of the deflectable tip.

26. The method of claim 23 wherein the deflectable tip is deflected through an angle of at least 90° relative to the shaft.

27. The method of claim 23 further comprising rotating the deflectable tip about a longitudinal axis parallel to the shaft without rotating a proximal end of the shaft.

28. The method of claim 27 wherein the deflectable tip is rotated such that a distal end of the tip remains generally within a plane perpendicular to the shaft.

29. A steerable electrophysiology catheter comprising:

a shaft with a first bending stiffness, the shaft having a proximal end, a distal end, and an axial lumen therebetween;

a deflectable tip with a second bending stiffness less than the first bending stiffness, the deflectable tip having a proximal end secured to the distal end of the shaft, a distal end, a first radially offset axial tip lumen, a second axial tip lumen and a third axial tip lumen, each of said first, second and third axial tip lumens being in communication with the axial lumen of the shaft;

at least one electrode secured to the deflectable tip;

means for delivering current from the proximal end of the shaft to the electrode;

a manipulator wire extending through the axial lumen of the shaft and the first axial tip lumen, the manipulator wire having a distal end secured to the distal end of the deflectable tip and a proximal end near the proximal end of the shaft;

means at the proximal end of the shaft for applying axial force to the manipulator wire to deflect the deflectable tip into a first curvature;

a core wire disposed in the axial lumen of the shaft and the second axial tip lumen, the core wire having a distal end secured to the distal end of the deflectable tip and a proximal end near the proximal end of the shaft;

means for exerting torque on the proximal end of the core wire so to rotate the deflectable tip about a longitudinal axis without rotating the proximal end of the shaft;

a stiffener wire slidably disposed in the axial lumen of the shaft and the third axial tip lumen; and means at the proximal end of the shaft for axially moving the stiffener wire relative to the deflectable tip such that at least a portion of the deflectable tip assumes a second curvature.

30. The catheter of claim 29 wherein the core wire has a distal portion having a cross-sectional width and thickness, the width being substantially greater than the thickness.

31. The catheter of claim 29 wherein the second axial lumen has a cross-sectional width and height, the width being substantially greater than the height so as to prevent rotation of the distal portion of the core wire relative to the distal tip.

32. The catheter of claim 29 wherein the proximal end of the tip is secured to the core wire so to transmit torque from the core wire to the tip at the proximal end of the tip.

33. The catheter of claim 32 wherein the distal portion of the core wire has first and second sections with first and second cross-sectional widths and thicknesses.

34. A steerable electrophysiology catheter comprising:

a handle;

a shaft with a first bending stiffness, the shaft having a proximal end secured to the handle, a distal end, and an axial lumen therebetween;

a deflectable tip with a second bending stiffness less than the first bending stiffness, the deflectable tip having a proximal end secured to the distal end of the shaft, a distal end and an axial tip lumen in communication with the axial lumen of the shaft;

at least one electrode secured to the deflectable tip;

means for conducting current between the proximal end of the shaft and the electrode;

a manipulator wire extending through the axial lumen of the shaft and the tip lumen, the manipulator wire having a distal end secured to the distal end of the deflectable tip and a proximal end near the proximal end of the shaft;

an elongate, flexible stiffener element slidably disposed in the axial lumen of the shaft and the tip lumen, the stiffener element having a proximal end and a third bending stiffness;

means, coupled to the handle, for applying axial force to the manipulator wire to deflect the deflectable tip into a first curvature;

means, including a first slide axially slidable on the handle and secured to the proximal end of the stiffener wire, for axially moving the stiffener element relative to the deflectable tip such that at least a portion of the deflectable tip assumes a second curvature;

the handle including an outer surface, opposite which the first slide is positioned, and an inner surface; and the stiffener element moving means including a ball and slider element secured to the first slide and positioned against the inner surface of the handle, the ball slider element having at least one low friction element in contact with the inner surface of the handle.

35. The catheter of claim 34 wherein the low friction elements are metal spherical elements.

* * * * *